United States Patent [19]

Atwal et al.

[11] Patent Number: 4,753,946

[45] Date of Patent: Jun. 28, 1988

[54] PYRIMIDINECARBOXYLIC ACID DERIVATIVES

[75] Inventors: Karnail Atwal, Cranbury; George C. Rovnyak, Hopewell, both of N.J.

[73] Assignee: E. R. Squibb & Sons, Inc., Princeton, N.J.

[21] Appl. No.: 36,047

[22] Filed: Apr. 8, 1987

[51] Int. Cl.[4] .................. A61K 31/505; C07D 239/22; C07D 401/06; C07D 417/06

[52] U.S. Cl. .................... 514/274; 514/212; 514/227.8; 514/232.8; 514/235.8; 544/295; 544/316; 544/318; 544/122; 544/60; 544/58.5; 544/58.4; 540/601

[58] Field of Search ............... 544/295, 316, 318, 122, 544/60, 58.5, 58.4; 540/601; 514/274, 222, 232, 212

[56] References Cited

U.S. PATENT DOCUMENTS 4,048,171 9/1977 Bossert et al. .................. 260/256.4
4,572,908 2/1986 Campbell et al. .................... 514/340

FOREIGN PATENT DOCUMENTS 0157219 9/1985 European Pat. Off. .
0202654 11/1986 European Pat. Off. .
204317 12/1986 European Pat. Off. .
3234684 3/1984 Fed. Rep. of Germany .
868030 5/1961 United Kingdom .

OTHER PUBLICATIONS

Khanina et al., "Synthesis and Pharmacological Investigation of Some Derivatives of 1,2,3,4-Tetrahydropyrimidine-5-Carboxylic Acid", Khim. Farm. Zh., vol. 12, pp. 1321–1323 (1978).

Konyukhov et al., "Synthesis and Investigation of Heterocyclo Derivatives with Biological Activity", Zh. Organ. Khim., vol. 1, No. 8, pp. 1487–1489 (1965).

*Primary Examiner*—John M. Ford
*Attorney, Agent, or Firm*—Lawrence S. Levinson; Theodore R. Furman, Jr.

[57] ABSTRACT

Pyridine compounds of the formula

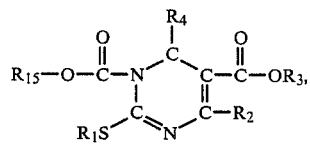

wherein $R_4$ is aryl or heterocyclo are disclosed. These compounds are useful as cardiovascular agents due to their calcium entry blocking vasodilator activity.

18 Claims, No Drawings

PYRIMIDINECARBOXYLIC ACID DERIVATIVES

FIELD OF THE INVENTION

The present invention relates to novel pyrimidinecarboxylic acid derivatives useful, for example, as antihypertensive agents.

BACKGROUND OF THE INVENTION

Bossert et al. in U.S. Pat. No. 4,048,171 disclose cardiovascular agents of the formula

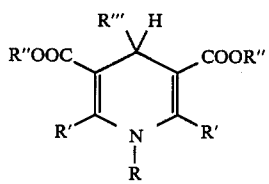

wherein
- R is hydrogen, straight, branched or cyclic lower alkyl, lower alkenyl, or lower alkinyl, unsubstituted or substituted; or benzyl, or phenethyl, unsubstituted or substituted in the aryl portion;
- R' is alkyl of 1 to 4 carbon atoms;
- R" is alkenyl of 2 to 6 carbon atoms, alkynyl of 2 to 6 carbon atoms, cyclic alkenyl of 3 to 6 carbon atoms interrupted by oxygen, alkenyl of 2 to 6 carbon atoms or alkynyl of 2 to 6 carbon atoms interrupted by 1 or 2 oxygen atoms, or alkenyl of 2 to 6 carbon atoms or alkinyl of 2 to 6 carbon atoms substituted by hydroxyl; and
- R''' is unsubstituted or substituted aryl; cyclohexyl; benzyl; styryl; pyridyl; pyrimidyl; furyl; thienyl; pyrrolyl; pyridyl; pyrrolyl, thienyl or furyl substituted by alkyl of 1 to 2 carbon atoms; or substituted pyrimidyl.

Stoltefuss et al., in German Offenlegungsschrift No. 3,234,684 A1, disclose dihydropyrimidines of the formula

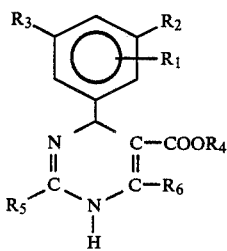

wherein $R_5$ is hydrogen, alkyl, substituted alkyl, phenyl, etc. These compounds possess cardiovascular activity.

Cho, et al, in European Application No. 0,157,219 A1, disclose dihydropyrimidine compounds useful as cardiovascular agents having the formula

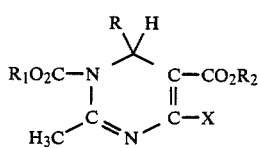

wherein $R_1$ is methyl or ethyl, $R_2$ is methyl or ethyl, R is phenyl or substituted phenyl and X is chloro or methyl.

SUMMARY OF THE INVENTION

In accordance with the present invention novel pyrimidine derivatives, useful, for example, as antihypertensive agents, are disclosed. These compounds have the formula

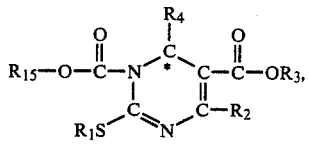

including a pharmaceutically acceptable salt thereof, wherein
$R_1$ is lower alkyl, lower alkenyl, lower alkynyl, —$(CH_2)_m$—cycloalkyl, —$(CH_2)_m$—aryl, —$(CH_2)_n$—heterocyclo, —$A_2$—OH, —$A_2$—O—lower alkyl, —$A_2$—O—$(CH_2)_m$—aryl, —$A_2$—SH, —$A_2$—S—lower alkyl, —$A_2$—S—$(CH_2)_m$—aryl,

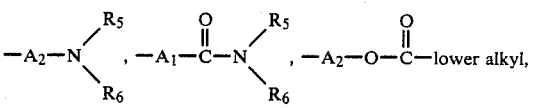

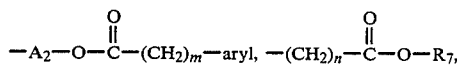

or halo substituted lower alkyl;

$R_2$ is hydrogen, lower alkyl, lower alkenyl, lower alkyl, cycloalkyl, aryl, —$A_1$—cycloalkyl, —$A_1$—aryl, —$A_1$—heterocyclo, —$A_1$—OH, —$A_1$—O—lower alkyl, —$A_1$—O—$(CH_2)_m$—aryl, —$A_1$—SH, —$A_1$—S—lower alkyl, —$A_1$—S—$(CH_2)_m$—aryl,

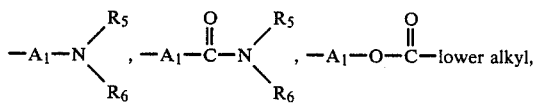

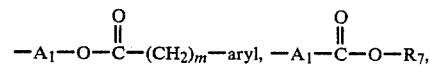

or halo substituted lower alkyl;

$R_3$ is hydrogen, lower alkyl, aryl, cycloalkyl, —$A_1$—aryl, —$A_1$—cycloalkyl, —$A_1$—heterocyclo, —$A_2$—OH, —$A_2$—O—lower alkyl, —$A_2$—O—$(CH_2)_m$—aryl, —$A_2$—SH, —$A_2$—S—lower alkyl, —$A_2$—S—$(CH_2)_m$—aryl,

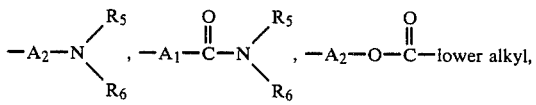

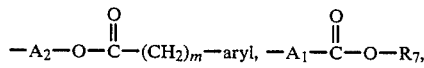

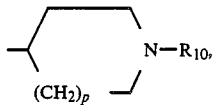

halo substituted lower alkyl, or a pharmaceutically acceptable salt forming ion;

$R_4$ is heterocyclo, mono substituted phenyl wherein said substituent is selected from the group consisting of lower alkyl of 1 to 4 carbons, halo, $CF_3$ and nitro, or disubstituted phenyl wherein said substituents are selected from the group consisting of methyl, halo, $CF_3$, and nitro;

$R_5$ and $R_6$ are independently selected from the group consisting of hydrogen, lower alkyl, —$(CH_2)_m$—aryl,

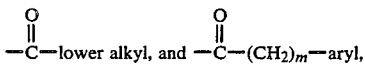

or $R_5$ and $R_6$ taken together with the N-atom to which they are attached complete a heterocyclic ring of the formula

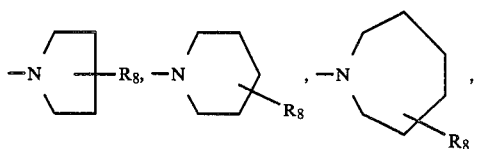

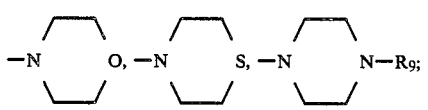

$R_7$ is hydrogen, lower alkyl, —$(CH_2)_m$—aryl or a pharmaceutically acceptable salt forming ion;

$R_8$ is hydrogen, lower alkyl of 1 to 4 carbons, lower alkoxy of 1 to 4 carbons, lower alkylthio of 1 to 4 carbons, halo, $CF_3$, nitro, or hydroxy;

$R_9$ is hydrogen, lower alkyl of 1 to 4 carbons,

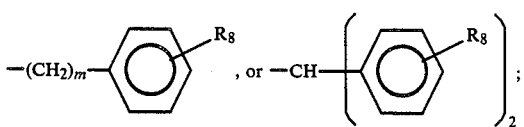

$R_{10}$ is lower alkyl of 1 to 4 carbons,

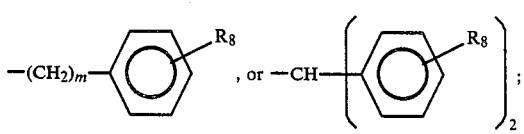

$A_1$ is

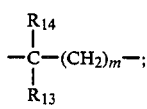

$A_2$ is

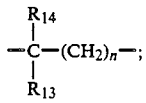

m is zero or an integer from 1 to 6;
n is an integer from 1 to 6;
p is zero, one or two;
$R_{13}$ and $R_{14}$ are independently selected from the group consisting of hydrogen, lower alkyl of 1 to 4 carbons,

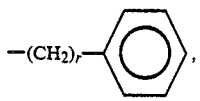

and —$(CH_2)_r$—cycloalkyl;

$R_{15}$ is lower alkyl, aryl, cycloalkyl, —$A_1$—aryl, —$A_1$—cycloalkyl, —$A_1$—heterocyclo, —$A_2$—OH, —$A_2$—O—lower alkyl, —$A_2$—O—$(CH_2)_m$—aryl, —$A_2$—SH, —$A_2$—S—lower alkyl, —$A_2$—S—$(CH_2)_m$—aryl,

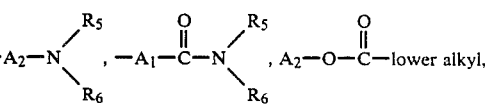

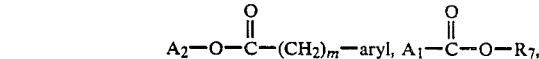

halo substituted lower alkyl, or

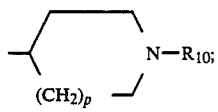

and,
r is zero or an integer from 1 to 3.

This invention is also directed to the novel pyrimidine compounds of formula I wherein $R_4$ is mono substituted phenyl wherein said substituent is selected from lower alkyl 1 to 4 carbons, halo, $CF_3$, and nitro, disubstituted phenyl wherein said substituents are selected from methyl, halo, $CF_3$, and nitro, or heterocyclo.

DETAILED DESCRIPTION OF THE INVENTION

This invention in its broadest aspects relates to the pyrimidine compounds of formula I above, to compositions and the method of using such compounds as cardiovascular agents.

The term lower alkyl used in defining various symbols refers to straight or branched chain hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated rings of 3 to 7 carbon atoms with cyclopentyl and cyclohexyl being most preferred.

The term halo refers to chloro, bromo and fluoro.

The term halo substituted lower alkyl refers to such lower alkyl grups described above in which one or more lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, —N-H—alkyl wherein alkyl is of 1 to 4 carbons, —N(alkyl)$_2$ wherein alkyl is of 1 to 4 carbons, $CF_3$, NCS, $OCHF_2$,

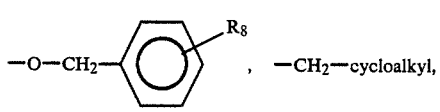, —CH$_2$—cycloalkyl,

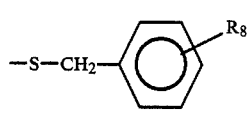

or —S—CH$_2$—cycloalkyl, and di-substituted phenyl, 1-naphthyl, or 2-naphthyl wherein said substituents are selected from methyl, methoxy, methylthio, halo, $CF_3$, nitro, amino, and $OCHF_2$.

The term heterocyclo refers to fully saturated or unsaturated monocyclic rings of 5 or 6 atoms containing one to four N atoms, or one O atom and up to two N atoms, or one S atom and up to two N atoms. The monocyclic ring is attached by way of an available carbon atom. Preferred monocyclic heterocyclo groups include 2- and 3-thienyl, 2- and 3-furyl, 2-, 3- and 4-pyridinyl, and imidazolyl. The term heterocyclo also includes bicyclic rings wherein the five or six membered monocyclic ring containing O, S and N atoms as defined above is fused to a benzene ring and the bicyclic ring is attached by way of an available carbon atom in the benzene ring. Preferred bicyclic heterocyclo groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl. The term heterocyclo also includes 2-, 3-, or 4-pyridinyl rings having a substituent on one available carbon selected from lower alkyl of 1 to 4 carbons, lower alkylthio of 1 to 4 carbons, and lower alkoxy of 1 to 4 carbons, especially 2-methylthio-3-pyridinyl.

The compounds of formula I wherein X is sulfur can be prepared by reacting an aldehyde of the formula $$R_4-CHO \qquad \text{II}$$

with a compound of the formula

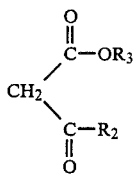 III to produce a keto ester of the formula

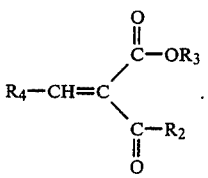 IV

Preferably this reaction is heated in the presence of piperidene and acetic acid. Compound IV is thereafter treated with a thiopseudourea of the formula

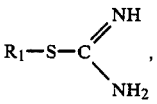 V particularly the hydrogen sulfate salt thereof, in the presence of a sodium bicarbonate or sodium acetate to give

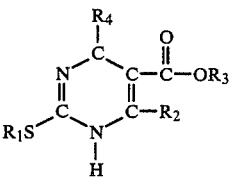 VI

The pyrimidinecarboxylic acid ester of formula VI is treated with phosgene in the presence of an organic base such as pyridine and thereafter reacted with an alcohol of the formula $$R_{15}-OH \qquad \text{VII}$$

to give the compound of formula I. This procedure is preferred when $R_{15}$ is

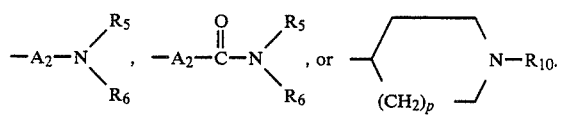

Compounds of formula VI can also be treated with chloroformate of the formula

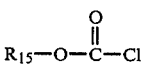 VIII to provide compounds of formula I.

Alternatively, compound II, compound III and a thiourea of the formula

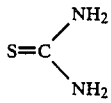  IX can be reacted in the presence of a solvent and hydrochloric acid to provide

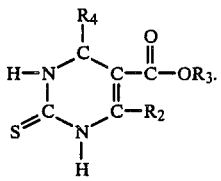  X

Compound X is treated with potassium carbonate and a compound of the formula

R₁—Br    XI in a solvent such as acetone to provide the compound of formula VI which is thereafter treated, as above, to provide compounds of formula I.

The compounds of formula I can also be prepared by reacting the alcohol of formula VII with 4-nitrophenyl chloroformate to give the reagent of the formula

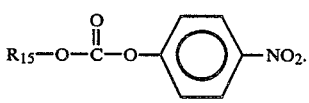  XII

The reagent of formula XII is then reacted with the pyrimidinecarboxylic acid ester of formula VI to provide compounds of formula I.

The compounds of formula I contain an asymmetric center within the pyrimidine ring as represented by the *. Thus, the compounds of formula I can exist in stereoisomeric forms or mixtures thereof. The above-described processes can utilize racemates, enantiomers or diastereomers as starting materials. When diastereomeric products are prepared, they can be separated by conventional chromatographic or fractional crystallization methods.

If any of $R_1$, $R_2$, $R_3$, $R_4$ and $R_{15}$ in the above are aryl, —$A_1$—aryl, or terminate in —$(CH_2)_m$—aryl wherein aryl is phenyl, 1-naphthyl, or 2-naphthyl substituted with one or more hydroxy or amino groups, heterocyclo, —$A_1$—heterocyclo or —$A_2$—heterocyclo wherein the heterocyclo ring contains an NH such as imidazolyl, or a substituted alkyl such as —$A_2$—OH, —$A_2$—$NH_2$, —$A_2$—SH, or

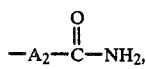

then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred pyrimidine derivatives of formula I are those wherein $R_{15}$ is straight or branched chain lower alkyl of 1 to 5 carbons, benzyl,

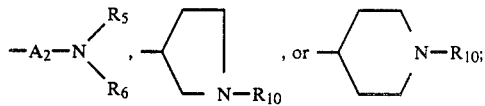

$R_1$ is lower alkyl of 1 to 5 carbons, lower alkenyl of 3 to 5 carbons or benzyl;

$R_2$ is straight or branched chain lower alkyl of 1 to 5 carbons, especially methyl;

$R_3$ is straight or branched chain lower alkyl of 1 to 5 carbons, benzyl,

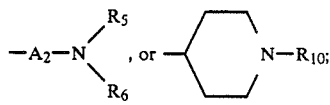

$R_4$ is mono substituted phenyl wherein said substituent is selected from lower alkyl of 1 to 4 carbons, halo, $CF_3$, or nitro, disubstituted phenyl wherein said substituents are selected from methyl, halo, $CF_3$ and nitro, 2-, 3-, or 4-pyridinyl, 2-methylthio-3-pyridinyl, or 2, 1, 3-benzoxadiazolyl;

$A_2$ is —$CH_2$—$(CH_2)_n$— or $$-CH-(CH_2)_n;\\ \ \ \ \ |\\ \ \ \ CH_3$$

n is 1, 2 or 3;

$R_5$ and $R_6$ are independently selected from hydrogen, straight or branched chain lower alkyl of 1 to 5 carbons, benzyl and —$(CH_2)_m$—aryl, or $R_5$ and $R_6$ taken together with the N atom to which they are attached complete a heterocyclic ring of the formula

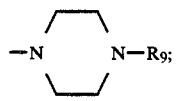

$R_9$ is methyl, benzyl, or diphenylmethyl; and,
$R_{10}$ is benzyl or diphenylmethyl.

Most preferred pyrimidine derivatives of formula I are those wherein $R_{15}$ is methyl, ethyl, isopropyl, benzyl,

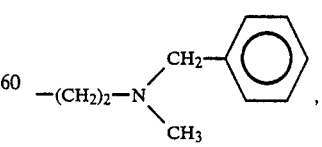

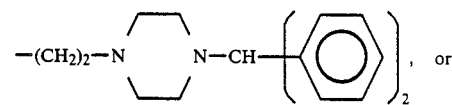

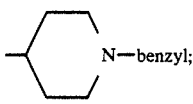

$R_1$ is methyl, pentyl, 2-propenyl or benzyl;
$R_2$ is methyl;
$R_3$ is ethyl, isopropyl, 1-methylpropyl,

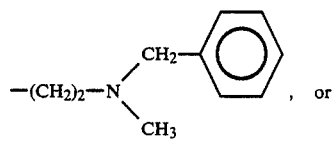

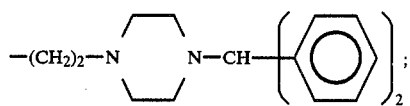

and, $R_4$ is 2-nitrophenyl, 3-nitrophenyl, 2-chlorophenyl, 3-chlorophenyl, 2-(trifluoromethyl)phenyl, 3-(trifluoromethyl)phenyl, 2,3-dichlorophenyl, 2-chloro-3-nitrophenyl, or 4-(2,1,3-benzoxadiazol)-yl.

The compounds of formula I which contain an amino group form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_{15}$, $R_2$ or $R_3$ is

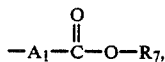

or in which $R_3$ is hydrogen, or in which $R_1$ is

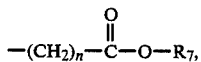

include carboxylic acid salts, i.e., $R_3$ or $R_7$ is a pharmaceutically acceptable salt forming ion. Preferred salt forming ions include alkali metal salt ions such as sodium, potassium and lithium, and alkaline earth metal salt ions such as calcium and magnesium.

The compounds of formula I and the pharmaceutically acceptable salts thereof are useful as cardiovascular agents. These compounds act as calcium entry blocking vasodilators and are especially useful as anti-hypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg per kilogram of body weight per day, preferably from about 1 to about 50 mg per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will be further described by reference to the following examples, however, it should not be limited by the details therein.

EXAMPLE 1

4-Methyl-2-(methylthio)-6-(3-nitrophenyl)-1,5(6H)-pyrimidinedicarboxylic acid, 1-[2-[methyl(phenylmethyl)amino]ethyl]5-(1-methylpropyl)ester, monohydrochloride

A.

2-(3-Nitrophenylmethylidene)-3-oxobutanoic acid, 1-methylpropyl ester

A solution of sec-butyl acetoacetate (5.0 g, 0.031 moles), 3-nitrobenzaldehyde (4.7 g, 0.031 moles), 0.5 ml of piperidine and 0.5 ml of acetic acid in 50 ml of benzene was heated at reflux for one hour collecting 1 eq. of water. The cooled solution, in ethyl acetate, was washed with sodium hydrogen carbonate, potassium hydrogen sulfate and brine, dried and evaporated to give 9.2 g of the title A compound as a dark oil.

B.

1,4-Dihydro-6-methyl-2-(methylthio)-4-(3-nitrophenyl)-5-pyrimidinecarboxylic acid, 3-methylpropyl ester, monohydrochloride A mixture of the title A compound (2.0 g, 0.0068 moles), 2-methyl-2-thiopseudourea sulfate (0.95 g, 0.0034 moles) and sodium acetate (0.56 g, 0.0068 moles) in 20 ml of dimethylformamide was stirred and heated for 4 hours at 70° C., cooled and diluted with ethyl acetate. The solution was washed with sodium hydrogen carbonate, water and brine, then dried and evaporated to give 2.4 g of an oil. Flash chromatography gave 1.16 g of the title B compound as a yellow solid, m.p. 107°–109°.

C.

4-Methyl-2-(methylthio)-6-(3-nitrophenyl)-1,5(6H)-pyrimidinedicarboxylic acid, 1-[2-[methyl(phenylmethyl)amino]ethyl]5-(1-methylpropyl)ester, monohydrochloride A mixture of the compound of part B (0.5 g, 1.25 mmol) in 5 ml of methylene chloride and 5 ml of pyridine under argon at room temperature was treated with triethylamine (175 μl, 127 mg, 1.25 mmol), cooled to between 0.20 and 5° C. and treated with phosgene (1.5 ml, 12.5% toluene solution, ca 1.87 mmol) over a 10 minute period. After stirring at room temperature for 0.5 hours, N-methyl-N-benzyethanolamine (0.31 g, 1.87 mmol) in 3 ml of methylene chloride was added and the mixture was stirred at room temperature overnight. Volatiles were stripped in vacuo and the residue, dissolved in ethyl acetate, was washed with sodium hydrogen carbonate, water and saturated brine. The aqueous washes were back extracted with fresh ethyl acetate. The combined organic fractions were dried over anhydrous magnesium sulfate and concentrated in vacuo. Flash chromatography yielded about 0.38 g of a free base which was thereafter dissolved in ethyl ether and treated with excess ethereal hydrochloric acid to give a gummy precipitate. The ethyl ether was decanted and replaced with hexane to provide 350 mg of the title compound as a fine, white non-hydroscopic powder, m.p. 75°–90°: tlc, silica gel, ethyl acetate/hexane (1:1), $R_f$=0.41.

Microanalysis Calc'd for $C_{28}H_{34}N_4O_6S \cdot HCl$: Calc'd: C 56.89; H, 5.97; N 9.48; Cl 6.00; S 5.43 Found: C 56.90; H 5.95; N 9.25; Cl 5.91; S 5.17.

EXAMPLE 2

4-Methyl-6-(3-nitrophenyl)-2-[(phenylmethyl)thio]-1,5(6H)-pyrimidinedicarboxylic acid, diethyl ester

A.

1,2,3,4-Tetrahydro-6-methyl-4-(3-nitrophenyl)-2-thioxo-5-pyrimidinecarboxylic acid, ethyl ester The solution containing m-nitrobenzaldehyde (7.55 g, 50.0 mmoles), ethyl-acetoacetate (6.5 g, 50.0 mmoles) and thiourea (3.8 g, 50.0 mmoles) in absolute ethanol (30 ml) was treated with concentrated hydrochloric acid (0.2 ml). The resulting reaction mixture was heated at reflux for 6 hours. It was then cooled to room temperature and triturated. A small amount of a white solid precipitated out. The reaction flask was then allowed to cool in the refrigerator overnight. The precipitate formed was filtered off and washed with more absolute ethanol to provide colorless solid (2.5 g). For analytical purposes, this material was recrystallized from absolute ethanol to give colorless crystals, m.p. 208°–209° C.

B.

1,4-Dihydro-6-methyl-4-(3-nitrophenyl)-2-[(phenylmethyl)thio]-5-pyrimidinecarboxylic acid, ethyl ester The suspension of the compound of part A (400 mg, 1.24 mmoles), potassium carbonate (270 mg, 2.0 mmoles) and benzyl bromide (240 mg, 1.4 mmoles) in acetone (7.0 ml) was stirred at room temperature overnight. The solid was filtered off and the filtrate was diluted with ethyl acetate. The solution was washed with water, brine and was dried over anhydrous magnesium sulfate. Evaporation of the solvent provided a light yellow solid which was triturated with isopropyl ether and filtered off (370 mg). This material was combined with another batch (150 mg) and recrystallized from isopropyl ether-dichloromethane to give light yellow crystals, m.p. 129°–130° C.

C.

4-Methyl-6-(3-nitrophenyl)-2-[(phenylmethyl)thio]-1,5(6H)-pyrimidinecarboxylic acid, diethyl ester The suspension of the compound of part B (1.0 g, 2.40 mmoles) in methylene chloride (10 ml) was treated at 0° C. with pyridine (0.5 ml) followed by ethylchloroformate (320 mg, 3.0 mmoles). The ice bath was removed and the reaction was allowed to stir at room temperature for 30 minutes. It was then diluted with ethyl acetate and the resulting solution was washed with 5 percent citric acid, sodium bicarbonate solution and brine. After drying over anhydrous magnesium sulfate, the solvent was stripped off to give a yellow foam. Crystallization from isopropyl ether provided light yellow crystalline product (600 mg). The mother liquor was concentrated and crystallized from ether-hexanes to give a second crop (384 mg). Both crops were combined and triturated with ether-hexanes to provide the title compound as light yellow solid, m.p. 90.5°–92° C.

Microanalysis Calc'd for $C_{24}H_{25}N_3O_6S$: Calc'd: C 59.61; H 5.21; N 8.69; S 6.63; Found: C 59.64; H 5.27; N 8.75; S 6.72.

EXAMPLES 3–17

Using the procedures outlined above and in the first two examples, the following compounds within the scope of the present invention can be made.

| Ex. No. | $R_1$ | $R_2$ | $R_3$ | $R_4$ | $R_{15}$ |
|---|---|---|---|---|---|
| 3 | —CH$_2$—CH=CH$_2$ | —CH$_3$ | —CH$_2$—C$_6$H$_5$ | thienyl | —CH$_2$—C$_6$H$_5$ |
| 4 | —CH$_2$—CH=CH$_2$ | —C$_2$H$_5$ | —CH$_2$—cyclohexyl | pyridyl | —CH$_2$—cyclohexyl |
| 5 | —CH$_2$—CH=CH$_2$ | —CH$_3$ | —(CH$_2$)$_2$—pyridyl | 2-NO$_2$-C$_6$H$_4$ | —(CH$_2$)$_2$—pyridyl |
| 6 | —CH$_2$—CH=CH$_2$ | —CH$_3$ | —(CH$_2$)$_2$—O—CH$_3$ | 2-CF$_3$-C$_6$H$_4$ | —(CH$_2$)$_2$—O—CH$_3$ |
| 7 | —CH$_2$—CH=CH$_2$ | —CH$_3$ | —(CH$_2$)$_2$—O—C$_6$H$_5$ | 2-NO$_2$-3-Cl-C$_6$H$_3$ | —(CH$_2$)$_2$—O—C$_6$H$_5$ |
| 8 | —CH$_2$—C$_6$H$_5$ | —CH$_3$ | —(CH$_2$)$_2$—S—C$_2$H$_5$ | 2,3-Cl$_2$-C$_6$H$_3$ | —(CH$_2$)$_2$—S—C$_2$H$_5$ |

-continued

Structure:
$$R_{15}-O-\overset{O}{\overset{\|}{C}}-\underset{\underset{\overset{\|}{O}}{N}}{N}\overset{R_4}{\underset{R_{15}}{\overset{|}{C}}}\overset{\overset{O}{\|}}{\underset{R_2}{C}}-OR_3$$

| Ex. No. | $R_1$ | $R_2$ | $R_3$ | $R_4$ | $R_{15}$ |
|---|---|---|---|---|---|
| 9 | —CH$_2$—(cyclohexyl) | —CH$_2$—(phenyl) | —CH(CH$_3$)$_2$ | 2-nitrophenyl | —(CH$_2$)$_2$—N(CH$_3$)$_2$ |
| 10 | —(CH$_2$)$_2$—S—(phenyl) | —CH$_3$ | —CH(CH$_3$)$_2$ | 2,3-difluorophenyl | —(CH$_2$)$_2$—N(piperazinyl)-phenyl |
| 11 | —(CH$_2$)$_4$—CH$_3$ | —CH$_3$ | —CH(CH$_3$)$_2$ | pyridyl | —CH$_2$—C(=O)—N(morpholinyl) |
| 12 | —CH$_2$CH$_2$CH=CH$_2$ | —CH$_3$ | —(CH$_2$)$_2$—O—$\overset{O}{\overset{\|}{C}}$—C$_2$H$_5$ | 2-nitrophenyl | —(CH$_2$)$_2$—O—$\overset{O}{\overset{\|}{C}}$—C$_2$H$_5$ |
| 13 | —CH$_2$CH=CH$_2$ | —CH$_3$ | —(CH$_2$)$_2$—O—$\overset{O}{\overset{\|}{C}}$—CH$_2$—(phenyl) | (naphthyl)-CF$_3$ | —C$_2$H$_5$ |

-continued $$R_{15}-O-\underset{\underset{O}{\|}}{C}-\underset{\underset{R_{1}S}{|}}{\overset{\overset{R_{4}}{|}}{N}}-\underset{\underset{O}{\|}}{C}-\overset{\overset{O}{\|}}{\underset{\underset{R_{2}}{|}}{C}}-OR_{3}$$

| Ex. No. | $R_1$ | $R_2$ | $R_3$ | $R_4$ | $R_{15}$ |
|---|---|---|---|---|---|
| 14 | —CH$_2$—C$_6$H$_5$ | —CH$_3$ | —(CH$_2$)$_2$—C(=O)—O—C$_2$H$_5$ | 2,3-dichlorophenyl | —(CH$_2$)$_2$—C(=O)—O—C$_2$H$_5$ |
| 15 | —CH$_2$—C$_6$H$_5$ | —CH$_3$ | —C$_2$H$_5$ | —CH=N—CH=CH—N(CH$_2$C$_6$H$_5$)— (imidazole-CH$_2$Ph) | —C$_2$H$_5$ |
| 16 | —CH$_3$ | —CH$_3$ | —C$_2$H$_5$ | N-benzyl-methylindolyl | —C$_2$H$_5$ |
| 17 | —CH$_3$ | —CH$_3$ | —CH$_3$ | methylbenzonitrile | —CH(CH$_3$)$_2$ |

What is claimed is:

1. A compound of the formula $$R_{15}-O-\overset{O}{\overset{\|}{C}}-\overset{R_4}{\overset{|}{N}}-\overset{}{\underset{R_1S-C=N}{C}}-\overset{O}{\overset{\|}{C}}-OR_3,$$

including a pharmaceutically acceptable salt thereof, wherein $R_1$ is lower alkyl, lower alkenyl, lower alkynyl, $-(CH_2)_m$—cycloalkyl, $-(CH_2)_q$—aryl, $-A_2$—OH, $-A_2$—O—lower alkyl, $-A_2$—O—$(CH_2)_m$—aryl, $-A_2$—SH, $-A_2$—S—lower alkyl, $-A_2$—S—$(CH_2)_m$—aryl, $$-A_2-N\overset{R_5}{\underset{R_6}{\diagdown}}, -A_1-\overset{O}{\overset{\|}{C}}-N\overset{R_5}{\underset{R_6}{\diagdown}}, -A_2-O-\overset{O}{\overset{\|}{C}}-\text{lower alkyl},$$

$$-A_2-O-\overset{O}{\overset{\|}{C}}-(CH_2)_m-\text{aryl}, -(CH_2)_n-\overset{O}{\overset{\|}{C}}-O-R_7,$$

or halo substituted lower alkyl;

$R_2$ is hydrogen, lower alkyl, lower alkenyl, lower alkyl, cycloalkyl, aryl, $-A_1$—cycloalkyl, $-A_1$—aryl, $-A_1$—OH, $-A_1$—O—lower alkyl, $-A_1$—O—$(CH_2)_m$—aryl, $-A_1$—SH, $-A_1$—S—lower alkyl, $-A_1$—S—$(CH_2)_m$—aryl, $$-A_1-N\overset{R_5}{\underset{R_6}{\diagdown}}, -A_1-\overset{O}{\overset{\|}{C}}-N\overset{R_5}{\underset{R_6}{\diagdown}}, -A_1-O-\overset{O}{\overset{\|}{C}}-\text{lower alkyl},$$

$$-A_1-O-\overset{O}{\overset{\|}{C}}-(CH_2)_m-\text{aryl}, -A_1-\overset{O}{\overset{\|}{C}}-O-R_7,$$

or halo substituted lower alkyl;

$R_3$ is hydrogen, lower alkyl, aryl, cycloalkyl, $-A_1$—aryl, $-A_1$—cycloalkyl, $-A_2$—OH, $-A_2$—O—lower alkyl, $-A_2$—O—$(CH_2)_m$—aryl, $-A_2$—SH, $-A_2$—S—lower alkyl, $-A_2$—S—$(CH_2)_m$—aryl, $$-A_2-N\overset{R_5}{\underset{R_6}{\diagdown}}, -A_1-\overset{O}{\overset{\|}{C}}-N\overset{R_5}{\underset{R_6}{\diagdown}}, -A_2-O-\overset{O}{\overset{\|}{C}}-\text{lower alkyl},$$

$$-A_2-O-\overset{O}{\overset{\|}{C}}-(CH_2)_m-\text{aryl}, -A_1-\overset{O}{\overset{\|}{C}}-O-R_7,$$

$$\underset{(CH_2)_p}{\overset{\frown}{\diagdown}}N-R_{10},$$

halo substituted lower alkyl, or a pharmaceutically acceptable salt forming ion;

$R_4$ is mono substituted phenyl wherein said substituent is selected from the group consisting of lower alkyl of 1 to 4 carbons, halo, $CF_3$ and nitro, or disubstituted phenyl wherein said substituents are selected from the group consisting of methyl, halo, $CF_3$, and nitro;

$R_5$ and $R_6$ are independently selected from the group consisting of hydrogen, lower alkyl, $-(CH_2)_m$—aryl, $$-\overset{O}{\overset{\|}{C}}-\text{lower alkyl, and } -\overset{O}{\overset{\|}{C}}-(CH_2)_m-\text{aryl},$$

or $R_5$ and $R_6$ taken together with the N-atom to which they are attached complete a heterocyclic ring of the formula $$-N\overset{\frown}{\diagdown}R_8, -N\overset{\frown}{\diagdown}_{R_8}, -N\overset{\frown}{\diagdown}_{R_8},$$

$$-N\overset{\frown}{\diagdown}O, -N\overset{\frown}{\diagdown}S, -N\overset{\frown}{\diagdown}N-R_9;$$

$R_7$ is hydrogen, lower alkyl, $-(CH_2)_m$—aryl or a pharmaceutically acceptable salt forming ion;

$R_8$ is hydrogen, lower alkyl of 1 to 4 carbons, lower alkoxy of 1 to 4 carbons, lower alkylthio of 1 to 4 carbons, halo, $CF_3$, nitro, or hydroxy;

$R_9$ is hydrogen, lower alkyl of 1 to 4 carbons, $$-(CH_2)_m-\bigcirc-R_8, \text{ or } -CH-\left\{\bigcirc-R_8\right\}_2;$$

$R_{10}$ is lower alkyl of 1 to 4 carbons, $$-(CH_2)_m-\bigcirc-R_8, \text{ or } -CH-\left\{\bigcirc-R_8\right\}_2;$$

$A_1$ is $$-\overset{R_{14}}{\underset{R_{13}}{\overset{|}{C}}}-(CH_2)_m-;$$

$A_2$ is $$-\overset{R_{14}}{\underset{R_{13}}{\overset{|}{C}}}-(CH_2)_n-;$$

m is zero or an integer from 1 to 6;
n is an integer from 1 to 6;
p is zero, one or two;
q is an integer from 3 to 6;

$R_{13}$ and $R_{14}$ are independently selected from the group consisting of hydrogen, lower alkyl of 1 to 4 carbons,

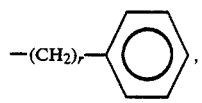

and $-(CH_2)_r-$cycloalkyl;

$R_{15}$ is lower alkyl, aryl, cycloalkyl, $-A_1-$aryl, $-A_1-$cycloalkyl, $-A_2-$OH, $-A_2-$O$-$lower alkyl, $-A_2-$O$-(CH_2)_m-$aryl, $-A_2-$SH, $-A_2-$S$-$lower alkyl, $-A_2-$S$-(CH_2)_m-$aryl,

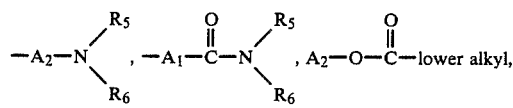

halo substituted lower alkyl, or

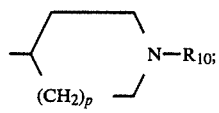

r is zero or an integer from 1 to 3; and the term "cycloalkyl" refers to saturated rings of 3 to 7 carbons;

the term "aryl" refers to phenyl, 1-naphthyl or 2-naphthyl, and mono substituted phenyl, 1-naphthyl or 2-naphthyl wherein said substituent is lower alkyl of 1 to 4 carbons, lower alkoxy of 1 to 4 carbons, lower alkylthio of 1 to 4 carbons, halo, nitro, cyano, hydroxy, amino, $-NH-$alkyl wherein alkyl is of 1 to 4 carbons, $-N$(alkyl)$_2$, wherein alkyl is of 1 to 4 carbons, $-CF_3$, $-NCS$, $-OCHF_2$,

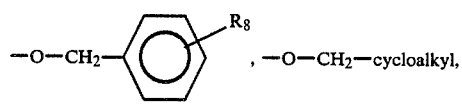

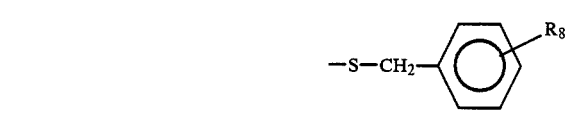

or $-S-CH_2-$cycloalkyl, and di-substituted phenyl, 1-naphthyl, or 2-naphthyl wherein said substituents are selected from the group consisting of methyl, methoxy, methylthio, halo, $CF_3$, nitro, amino, and $OCHF_2$.

2. The compound of claim 1 wherein $R_4$ is mono substituted phenyl wherein said substituent is selected from lower alkyl 1 to 4 carbons, halo, $CF_3$, and nitro, disubstituted phenyl wherein said substituents are selected from methyl, halo, $CF_3$, and nitro.

3. A compound of claim 1 wherein the term "lower alkyl" refers to straight or branched chain hydrocarbon radicals of one to eight carbons;

the term "lower alkenyl" refers to straight or branched chain hydrocarbon radicals of two to eight carbons with one double bond;

the term "lower alkynyl" refers to straight or branched chain hydrocarbon radicals of two to eight carbons with one triple bond; and, the term "halo" refers to chloro, bromo, and fluoro.

4. A compound of claim 1 wherein $R_{15}$ is straight or branched chain lower alkyl of 1 to 5 carbons, benzyl,

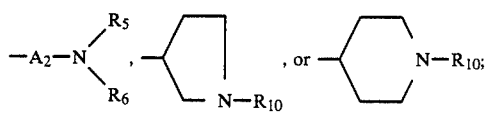

$R_1$ is lower alkyl of 1 to 5 carbons, lower alkenyl of 3 to 5 carbons, benzyl, or

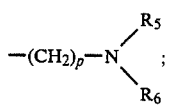

$R_2$ is straight or branched chain lower alkyl of 1 to 5 carbons, especially methyl;

$R_3$ is straight or branched chain lower alkyl of 1 to 5 carbons,

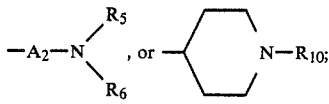

$R_4$ is mono substituted phenyl wherein said substituent is selected from lower alkyl of 1 to 4 carbons, halo, $CF_3$, or nitro, disubstituted phenyl wherein said substituents are selected from methyl, halo, $CF_3$ and nitro, 2-, 3-, or 4-pyridinyl, 2-methylthio-3-pyridinyl, or 2,1,3-benzoxadiazolyl;

$A_2$ is $-CH_2-(CH_2)_n-$ or

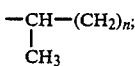

n is 1, 2 or 3;

$R_5$ and $R_6$ are independently selected from hydrogen, straight or branched chain lower alkyl of 1 to 5 carbons, benzyl and $-(CH_2)_m-$aryl, or $R_5$ and $R_6$ taken together with the N atom to which they are attached complete a heterocyclic ring of the formula

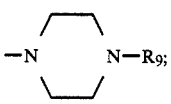

$R_9$ is methyl, benzyl, or diphenylmethyl; and, $R_{10}$ is benzyl or diphenylmethyl.

5. A compound of claim 4 wherein $R_{15}$ is methyl, ethyl, isopropyl, benzyl,

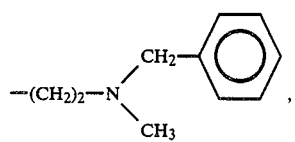

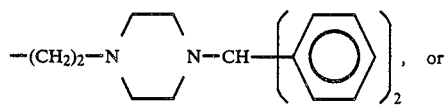

$R_1$ is methyl, pentyl, 2-propenyl or benzyl;
$R_2$ is methyl;
$R_3$ is ethyl, isopropyl, benzyl, 1-methylpropyl,

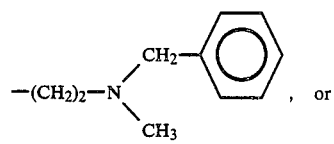

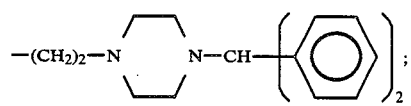

and,
$R_4$ is 2-nitrophenyl, 3-nitrophenyl, 2-chlorophenyl, 3-chlorophenyl, 2-(trifluoromethyl)phenyl, 3-(trifluoromethyl)phenyl, 2,3-dichlorophenyl, 2-chloro-3-nitrophenyl, or 4-(2,1,3-benzoxadiazol)-yl.

6. The compound of claim 5 wherein $R_{15}$ is

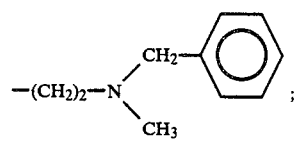

$R_1$ is methyl;
$R_2$ is methyl;
$R_3$ is 1-methylpropyl; and,
$R_4$ is 3-nitrophenyl.

7. The compound of claim 6 having the name 4-methyl-2-(methylthio)-6-(3-nitrophenyl)-1,5(6H)-pyrimidinedicarboxylic acid, 1-[2-[methyl(phenylmethyl)amino]ethyl]5-(1-methylpropyl)ester, monohydrochloride.

8. A composition useful in reducing blood pressure in a mammal comprising a pharmaceutically acceptable carrier and an anti-hypertensively effective amount of a compound or pharmaceutically acceptable salt thereof of the formula

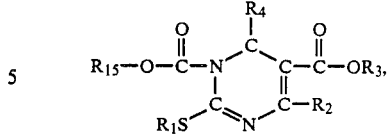

wherein $R_1$ is lower alkyl, lower alkenyl, lower alkynyl, $—(CH_2)_m—$cycloalkyl, $—(CH_2)_m—$aryl, $—A_2—OH$, $—A_2—O—$lower alkyl, $—A_2—O—(CH_2)_m—$aryl, $—A_2—SH$, $—A_2—S—$lower alkyl, $—A_2—S—(CH_2)_m—$aryl,

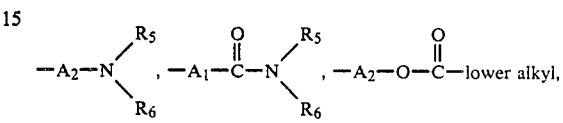

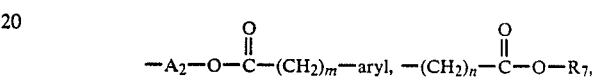

or halo substituted lower alkyl;
$R_2$ is hydrogen, lower alkyl, lower alkenyl, lower alkyl, cycloalkyl, aryl, $—A_1—$cycloalkyl, $—A_1—$aryl, $—A_1—OH$, $—A_1—O—$lower alkyl, $—A_1—O—(CH_2)_m—$aryl, $—A_1—SH$, $—A_1—S—$lower alkyl, $—A_1—S—(CH_2)_m—$aryl,

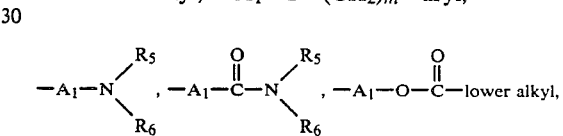

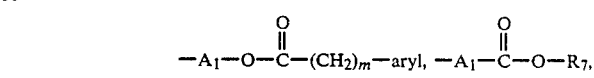

or halo substituted lower alkyl;
$R_3$ is hydrogen, lower alkyl, aryl, cycloalkyl, $—A_1—$aryl, $—A_1—$cycloalkyl, $—A_2—OH$, $—A_2—O—$lower alkyl, $—A_2—O—(CH_2)_m—$aryl, $—A_2—SH$, $—A_2—S—$lower alkyl, $—A_2—S—(CH_2)_m—$aryl,

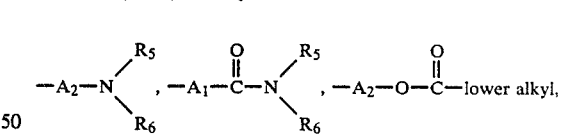

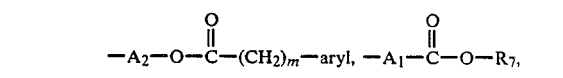

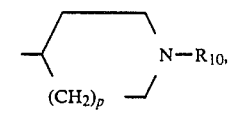

halo substituted lower alkyl, or a pharmaceutically acceptable salt forming ion;
$R_4$ is mono substituted phenyl wherein said substituent is selected from the group consisting of lower alkyl of 1 to 4 carbons, halo, $CF_3$ and nitro, or disubstituted phenyl wherein said substituents are selected from the group consisting of methyl, halo, $CF_3$, and nitro;

R5 and R6 are independently selected from the group consisting of hydrogen, lower alkyl, —(CH2)m—aryl,

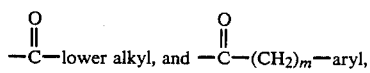

or R5 and R6 taken together with the N-atom to which they are attached complete a hetercyclic ring of the formula

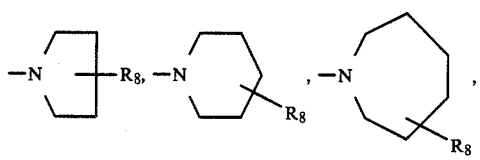

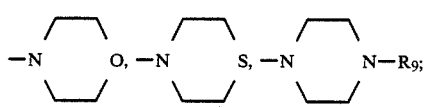

R7 is hydrogen, lower alkyl, —(CH2)m—aryl or a pharmaceutically acceptable salt forming ion;
R8 is hydrogen, lower alkyl of 1 to 4 carbons, lower alkoxy of 1 to 4 carbons, lower alkylthio of 1 to 4 carbons, halo, CF3, nitro, or hydroxy;
R9 is hydrogen, lower alkyl of 1 to 4 carbons,

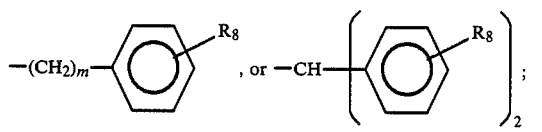

R10 is lower alkyl of 1 to 4 carbons,

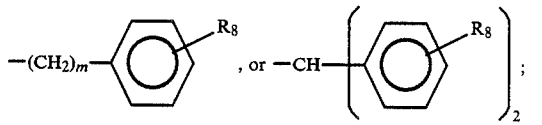

A1 is

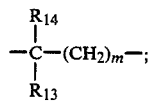

A2 is

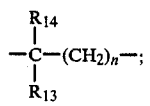

m is zero or an integer from 1 to 6;
n is an integer from 1 to 6;
p is zero, one or two;
q is an integer from 3 to 6;
R13 and R14 are independently selected from the group consisting of hydrogen, lower alkyl of 1 to 4 carbons,

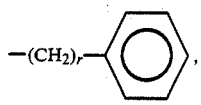

and —(CH2)r—cycloalkyl;
R15 is lower alkyl, aryl, cycloalkyl, —A1—aryl, —A1—cycloalkyl, —A1—heterocyclo, —A2—OH, —A2—O—lower alkyl, —A2—O—(CH2)m—aryl, —A2—SH, —A2—S—lower alkyl, —A2—S—(CH2)m—aryl,

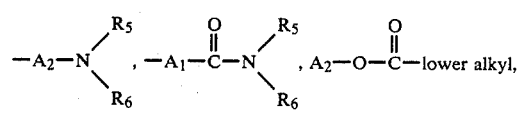

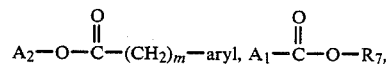

halo substituted lower alkyl, or

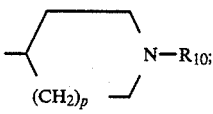

r is zero or an integer from 1 to 3; and
the term "cycloalkyl" refers to saturated rings of 3 to 7 carbons;
the term "aryl" refers to phenyl, 1-naphthyl or 2-naphthyl, and mono substituted phenyl, 1-naphthyl or 2-naphthyl wherein said substituent is lower alkyl of 1 to 4 carbons, lower alkoxy of 1 to 4 carbons, lower alkylthio of 1 to 4 carbons, halo, nitro, cyano, hydroxy, amino, —NH—alkyl wherein alkyl is of 1 to 4 carbons, —N(alkyl)2 wherein alkyl is of 1 to 4 carbons, —CF3, —NCS, —OCHF2,

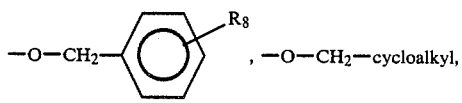

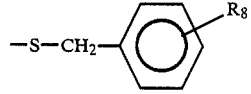

or —S—CH2—cycloalkyl, and di-substituted phenyl, 1-naphthyl, or 2-naphthyl wherein said substituents are selected from the group consisting of methyl, methoxy, methylthio, halo, CF3, nitro, amino, and OCHF2.

9. The composition of claim 8 wherein R4 is mono substituted phenyl wherein said substitutent is selected from the group consisting of lower alkyl of 1 to 4 carbons, lower alkoxy of 1 to 4 carbons, lower alkylthio of 1 to 4 carbons, halo, CF3, cyano, nitro, benzyloxy, and —OCHF2, disubstituted phenyl wherein said substituents are selected from the group consisting of methyl, methoxy, methylthio, halo, CFhd 3, and nitro.

10. The method of reducing blood pressure in a mammal comprising administering an effective amount of the composition of claim 8.

11. A composition of claim 8 wherein $R_4$ is mono substituted phenyl wherein said substituent is selected from lower alkyl 1 to 4 carbons, halo, $CF_3$, and nitro, disubstituted phenyl wherein said substituents are selected from methyl, halo, $CF_3$, and nitro.

12. A composition of claim 8 wherein
the term "lower alkyl" refers to straight or branched chain hydrocarbon radicals of one to eight carbons;
the term "lower alkenyl" refers to straight or branched chain hydrocarbon radicals of two to eight carbons with one double bond;
the term "lower alkynyl" refers to straight or branched chain hydrocarbon radicals of two to eight carbons with one triple bond; and,
the term "halo" refers to chloro, bromo, and fluoro.

13. A composition of claim 8 wherein
$R_{15}$ is straight or branched chain lower alkyl of 1 to 5 carbons, benzyl,

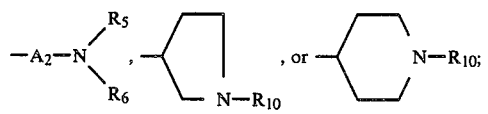

$R_1$ is lower alkyl of 1 to 5 carbons, lower alkenyl of 3 to 5 carbons, benzyl, or

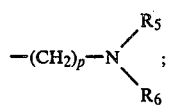

$R_2$ is straight or branched chain lower alkyl of 1 to 5 carbons, especially methyl;
$R_3$ is straight or branched chain lower alkyl of 1 to 5 carbons,

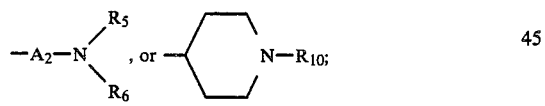

$R_4$ is mono substituted phenyl wherein said substituent is selected from lower alkyl of 1 to 4 carbons, halo, $CF_3$, or nitro, disubstituted phenyl wherein said substituents are selected from methyl, halo, $CF_3$ and nitro, 2-, 3-, or 4-pyridinyl, 2-methylthio-3-pyridinyl, or 2,1,3-benzoxadiazolyl;
$A_2$ is —$CH_2$—$(CH_2)_n$— or

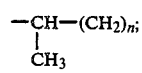

n is 1, 2 or 3;
$R_5$ and $R_6$ are independently selected from hydrogen, straight or branched chain lower alkyl of 1 to 5 carbons, benzyl and —$(CH_2)_m$—aryl, or $R_5$ and $R_6$ taken together with the N atom to which they are attached complete a heterocyclic ring of the formula

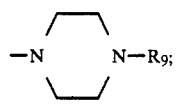

$R_9$ is methyl, benzyl, or diphenylmethyl; and,
$R_{10}$ is benzyl or diphenylmethyl.

14. A composition of claim 8 wherein
$R_{15}$ is methyl, ethyl, isopropyl, benzyl,

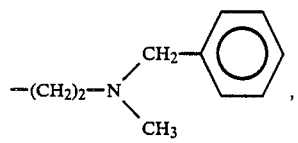

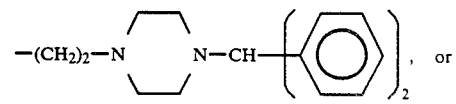

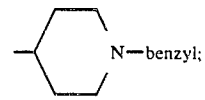

$R_1$ is methyl, pentyl, 2-propenyl or benzyl;
$R_2$ is methyl;
$R_3$ is ethyl, isopropyl, benzyl, 1-methylpropyl,

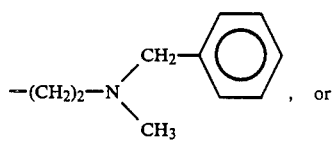

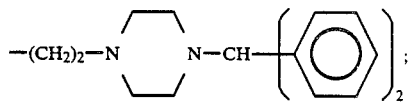

and,
$R_4$ is 2-nitrophenyl, 3-nitrophenyl, 2-chlorophenyl, 3-chlorophenyl, 2-(trifluoromethyl)phenyl, 3-(trifluoromethyl)phenyl, 2,3-dichlorophenyl, 2-chloro-3-nitrophenyl, or 4-(2,1,3-benzoxadiazol)-yl.

15. A composition of claim 8 wherein
$R_{15}$ is ethyl;
$R_1$ is benzyl;
$R_2$ is methyl;
$R_3$ is ethyl; and,
$R_4$ is 3-nitrophenyl.

16. A composition of claim 8 having the name 4-methyl-6-(3-nitrophenyl)-2-[(phenylmethyl)-thio]-1,5(6H)-pyrimidinedicarboxylic acid, diethyl ester.

17. A composition of claim 8 wherein
$R_{15}$ is

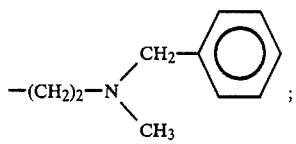
$R_1$ is methyl;
$R_2$ is methyl;
$R_3$ is 1-methylpropyl; and,
$R_4$ is 3-nitrophenyl.
18. A composition of claim 8 having the name 4-methyl-2-(methylthio)-6-(3-nitrophenyl)-1,5(6H)-pyrimidinedicarboxylic acid, 1-[2-[methyl(phenylmethyl)amino]ethyl] 5-(1-methyl-propyl)ester, monohydrochloride.
* * * * *